(12) United States Patent
Hoyme et al.

(10) Patent No.: US 9,031,652 B2
(45) Date of Patent: May 12, 2015

(54) USE CASE-BASED SERVICES

(71) Applicant: Cardiac Pacemakers, Inc., St. Paul, MN (US)

(72) Inventors: Kenneth P. Hoyme, Plymouth, MN (US); James Kalgren, Lino Lakes, MN (US); John LaLonde, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 45 days.

(21) Appl. No.: 13/892,632

(22) Filed: May 13, 2013

(65) Prior Publication Data

US 2014/0058468 A1    Feb. 27, 2014

Related U.S. Application Data

(60) Provisional application No. 61/693,402, filed on Aug. 27, 2012.

(51) Int. Cl.
*A61N 1/00* (2006.01)
*A61N 1/372* (2006.01)
*G06F 21/31* (2013.01)
*H04L 9/32* (2006.01)

(52) U.S. Cl.
CPC ........ *A61N 1/37217* (2013.01); *A61N 1/37235* (2013.01); *A61N 1/37252* (2013.01); *G06F 21/31* (2013.01); *H04L 9/3226* (2013.01); *H04L 2209/88* (2013.01)

(58) Field of Classification Search
USPC ....................................... 607/4–5, 30, 59–60
See application file for complete search history.

(56) References Cited

U.S. PATENT DOCUMENTS

| | | | |
|---|---|---|---|
| 5,488,410 | A | 1/1996 | Lieberfarb et al. |
| 6,083,248 | A | 7/2000 | Thompson |
| 6,386,882 | B1 | 5/2002 | Linberg |
| 6,678,560 | B1 | 1/2004 | Gilkerson et al. |
| 6,740,075 | B2 | 5/2004 | Lebel et al. |
| 6,804,554 | B2 | 10/2004 | Ujhelyi et al. |
| 6,810,290 | B2 | 10/2004 | Lebel et al. |

(Continued)

FOREIGN PATENT DOCUMENTS

WO    WO-2012063154 A1    5/2012

OTHER PUBLICATIONS

"International Application Serial No. PCT/US2013/040736, International Search Report mailed Aug. 29, 2013", 6 pgs.

(Continued)

*Primary Examiner* — Rex R Holmes
(74) *Attorney, Agent, or Firm* — Schwegman Lundberg & Woessner, P.A.

(57) ABSTRACT

An apparatus comprises an external device for communication with an implantable device. The external device includes a communication circuit configured to receive a communication signal from at least a third device separate from the external device and the implantable device, a locating circuit configured to determine a location of the external device using the received communication signal, a port configured to receive user identity information into the external device, and a control circuit electrically coupled to the communication circuit, the locating circuit, and the port. The control circuit is configured to allow user access to an implantable device feature according to the determined location and received user identity information.

8 Claims, 4 Drawing Sheets

(56) References Cited

U.S. PATENT DOCUMENTS

| | | | |
|---|---|---|---|
| 7,043,305 | B2 | 5/2006 | Kenknight et al. |
| 7,167,755 | B2 | 1/2007 | Seeberger et al. |
| 7,270,633 | B1 | 9/2007 | Goscha et al. |
| 7,273,457 | B2 | 9/2007 | Penner |
| 7,565,197 | B2 * | 7/2009 | Haubrich et al. ............... 607/30 |
| 7,630,773 | B2 | 12/2009 | Seeberger et al. |
| 7,641,619 | B2 | 1/2010 | Penner |
| 7,805,199 | B2 | 9/2010 | KenKnight et al. |
| 7,890,180 | B2 | 2/2011 | Quiles |
| 2005/0204134 | A1* | 9/2005 | Von Arx et al. ............... 713/168 |
| 2005/0288736 | A1 | 12/2005 | Persen et al. |
| 2006/0253301 | A1 | 11/2006 | Simms et al. |
| 2006/0287693 | A1 | 12/2006 | Kraft et al. |
| 2007/0288069 | A1 | 12/2007 | Goscha et al. |
| 2008/0244717 | A1 | 10/2008 | Jelatis et al. |
| 2009/0058636 | A1* | 3/2009 | Gaskill et al. ............ 340/539.11 |
| 2009/0063187 | A1 | 3/2009 | Johnson |
| 2010/0049279 | A1 | 2/2010 | Seeberger |
| 2011/0098788 | A1 | 4/2011 | Quiles |
| 2011/0145588 | A1 | 6/2011 | Stubbs et al. |
| 2014/0058383 | A1 | 2/2014 | Hoyme et al. |

OTHER PUBLICATIONS

"International Application Serial No. PCT/US2013/040736, Invitation to Pay Additional Fees and Partial Search Report mailed Sep. 10, 2013", 5 pgs.

"International Application Serial No. PCT/US2013/040736, Written Opinion mailed Aug. 29, 2013", 7 pgs.

* cited by examiner

USE CASE-BASED SERVICES

CLAIM OF PRIORITY

This application claims the benefit of priority under 35 U.S.C. §119(e) of Hoyme et al., U.S. Provisional Patent Application Ser. No. 61/693,402, entitled "USE CASE-BASED SERVICES", filed on Aug. 27, 2012, which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

IMDs can be sophisticated devices that can provide many advanced functions. External devices, such as IMD programmers, can communicate with an IMD using wireless telemetry and can be used to set device parameters. IMDs can also provide diagnostic data from one or more physiologic sensors. The programmers or other external devices can also be used to collect diagnostic data obtained by one or more physiologic sensors of the IMD.

Previously, a user of an external device that interacted with an IMD had expert knowledge of the IMD and external device. Presently, the functionality associated with personal electronic devices is ever-increasing (e.g., the ability for such electronic devices to communicate remotely), and it may be desirable to incorporate these functions into external devices that interact with IMDs. A result of this may be that users of the external device may wish to use different features of the IMD and that the users have diverse backgrounds that have qualifications to use the different device features.

Interfaces to interact with these types of devices can be difficult to follow for someone who only occasionally has to access the device. Therefore, it is desirable to simplify interactions as these devices become complicated. Also, it may be desirable to prevent unqualified users from having access to some of the device features. Therefore, it may be desirable to limit access to some device features.

OVERVIEW

This document relates generally to systems, devices, and methods for communication among an implantable device and external devices.

An apparatus example includes an external device for communication with an implantable device. The external device includes a communication circuit configured to receive a communication signal from at least a third device separate from the external device and the implantable device, a locating circuit configured to determine a location of the external device using the received communication signal, a port configured to receive user identity information into the external device, and a control circuit electrically coupled to the communication circuit, the locating circuit, and the port. The control circuit is configured to allow user access to an implantable device feature according to the determined location and received user identity information.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

Figure 1:
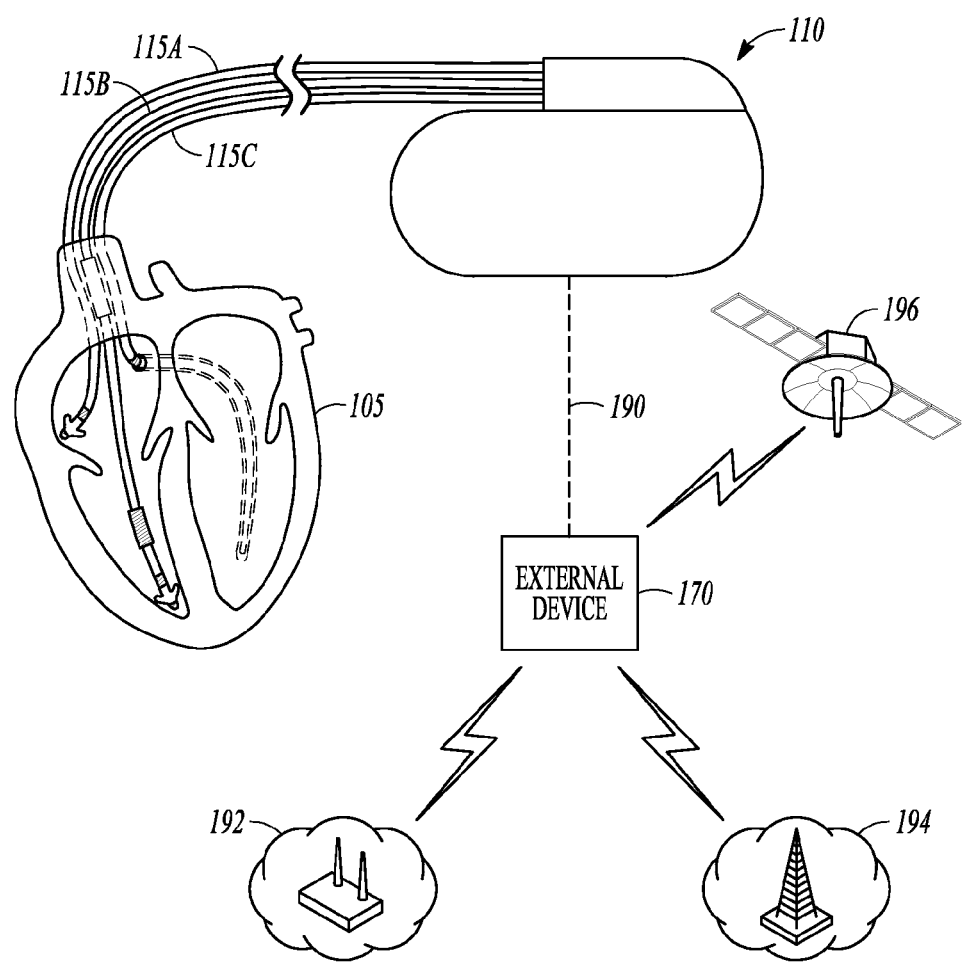
FIG. 1 is an illustration of an example of portions of a system that includes an IMD.

FIG. 1 is an illustration of an example of portions of a system that includes an IMD 110. Examples of IMD 110 include, without limitation, a pacemaker, a defibrillator, a cardiac resynchronization therapy (CRT) device, or a combination of such devices. The system 100 also typically includes an external device 170, such as an IMD programmer, that communicates wireless signals 190 with the IMD 110, such as by using radio frequency (RF) or other telemetry signals.

The IMD 110 can be coupled by one or more leads 115A-C to heart 105. Cardiac leads 115A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. Sensed electrical cardiac signals can be sampled to create an electrogram. An electrogram can be analyzed by the IMD and/or can be stored in the IMD 110 and later communicated to the external device 170 where the sampled signals can be displayed for analysis.

The functions needed to be performed by an external device can be tied to location. Therefore, user interaction with the IMD can be simplified if the user interface only includes those functions tied to a given location. Some locations may include users of diverse backgrounds and the users should be given different rights to different sets of features of the IMD.

Figure 2:
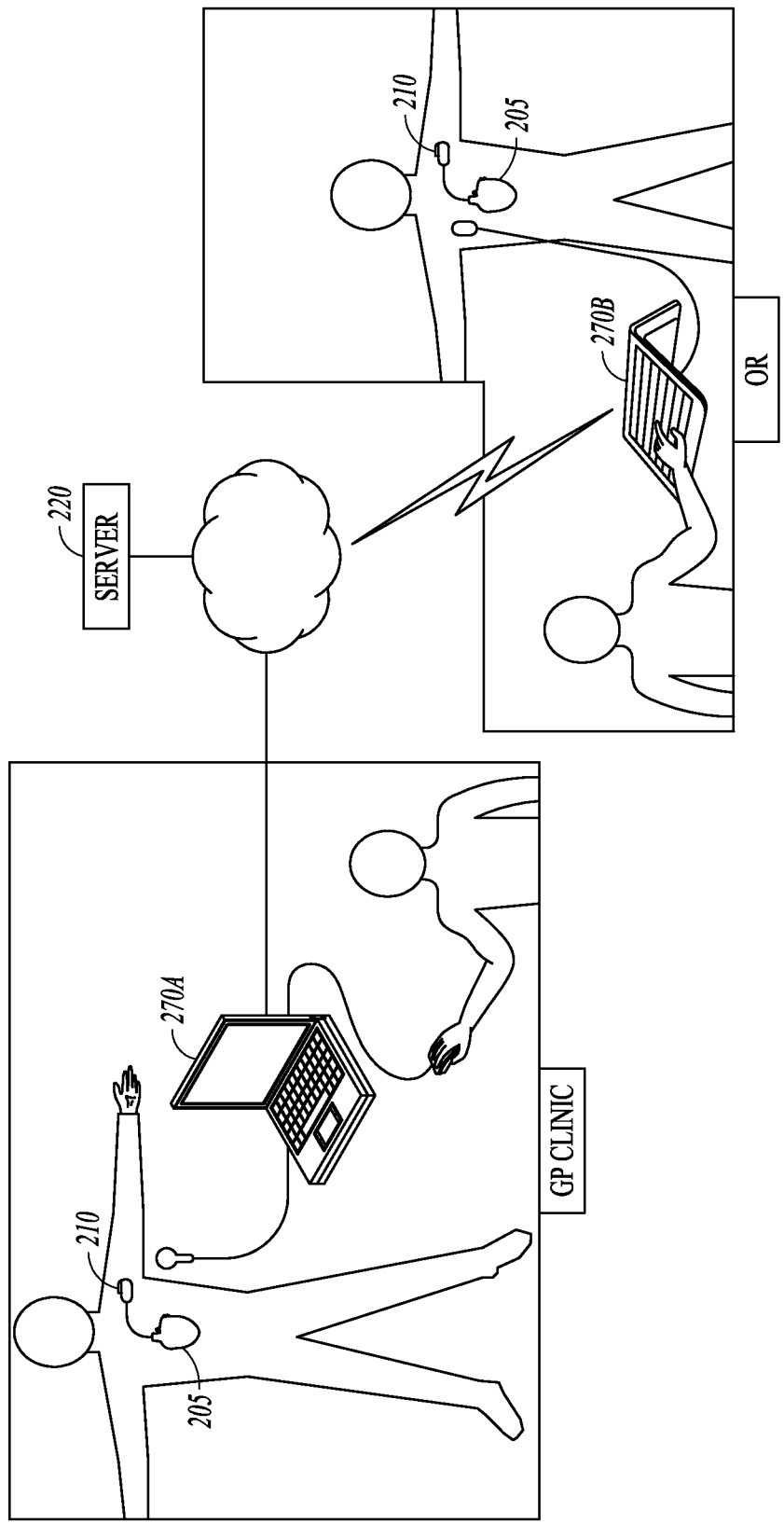
FIG. 2 is an illustration representing programming an IMD at different locations by different users of an external device.

FIG. 2 is an illustration representing programming an IMD at different locations by different users of an external device 270A, 270B. One of the locations may be a general practice (GP) clinic. An external device 270A, 270B is used to program an IMD 210. Functionality at the general practice clinic may only require that certain information be read from the IMD 210 (e.g., for analysis by the physician or for uploading to one or more servers 220 remote from the general practice clinic), while functionality at a cardiologist's office may require full programming capability. The services required at the general practice clinic can be much more limited than the services required at the cardiologist's office and the user interface for the external device 270A, 270B can therefore be greatly simplified when the external device 270A, 270B is located at the general practice clinic. In another example, the location is an operating room (OR) and the IMD 210 may be an ICD. The required functionality of the user interface of the external device 270A, 270B may only be to turn defibrillation detection and therapy in the IMD 210 off and on.

It can be seen that the capabilities provided by the external device 270 can be changed based on the location of the device. If the external device 270A, 270B is able to determine its location, the user interface of the external device 270A, 270B can be automatically tailored and often simplified to meet the requirements of the location.

Additionally, access to features of a device located at the general practice clinic may be different for different personnel (e.g., a nurse at a general practice clinic or technician at an MRI clinic may be given access to a different subset of features than a doctor). Thus, the user interface can be even more simplified based on user role information. Access to features at a location such as a cardiologist's office may require role or other identity information to be entered into the external device to ensure the qualifications of the user. Thus, entering identity information into the external device can also provide security to the access given to IMD device features.

Figure 3:
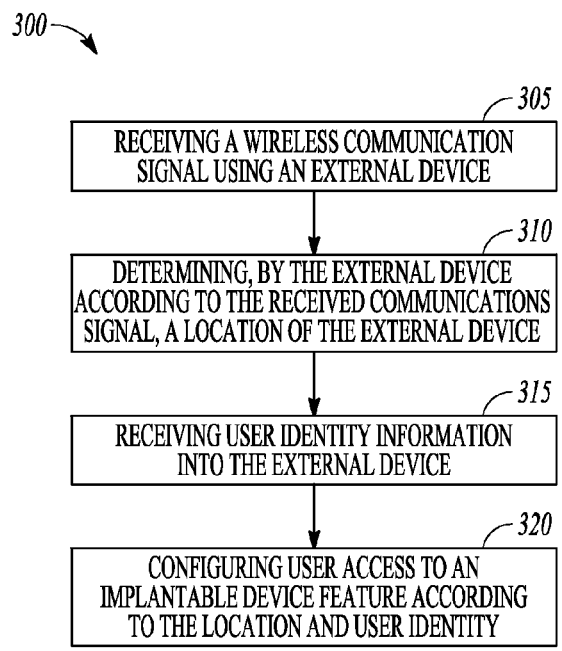
FIG. 3 is a flow diagram of an example of a method of providing varying medical device services based on location and a type of user.

FIG. 3 is a flow diagram of an example of a method 300 of providing varying medical device services based on location and a type of user. At block 305, a wireless communication signal is received using an external device. The external device can communicate with an implantable device (e.g., an IMD) and receive the wireless communication signal from at least a third device separate from the implantable device. As shown in FIG. 1, the wireless communication signal can be received from, among other things, a local area network (LAN) 192, a cellular telephone network 194, and a global positioning system (GPS) satellite 196. The wireless communication signal may be received using a communication circuit different from a telemetry circuit, or telemetry system, used for communication between the external device and the implantable device.

At block 310, the location of the external device is determined by the external device according to the received communication signal. The external device may also determine whether the location is associated with limiting functionality of the implantable device.

At block 315, user identity information is received into the external device, such as by an input port. The external device may determine whether the identity information corresponds to a user role associated with limiting functionality of the implantable device. At block 320, user access to implantable device features is configured by the external device according to the determined location and the received user identity information.

Figure 4:
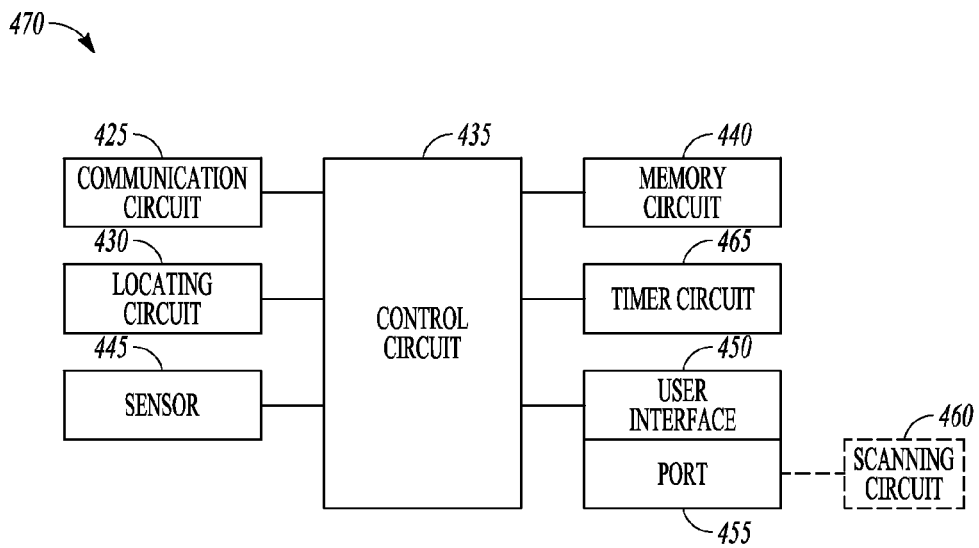
FIG. 4 is a block diagram of an example of portions of an external device for communication with an implantable device.

FIG. 4 is a block diagram of an example of portions of an external device 470 for communication with an implantable device. The external device 470 includes a communication circuit 425, a locating circuit 430, a port 455, and a control circuit 435 that is electrically coupled to the communication circuit 425, the locating circuit 430. In some examples, the communication circuit 425 includes a radio frequency (RF) receiver or transceiver. The communication circuit 425 receives a communication signal from at least one other device different from the implantable device, and the locating circuit 430 determines a location of the external device 470 using the received communication signal. The external device includes a port 455 to receive user identity information.

The control circuit 435 can include a microprocessor, a digital signal processor, application specific integrated circuit (ASIC), or other type of processor, interpreting or executing instructions in software modules or firmware modules. The control circuit 435 can include other circuits or sub-circuits to perform the functions described. These circuits may include software, hardware, firmware or any combination thereof. Multiple functions can be performed in one or more of the circuits or sub-circuits as desired.

The control circuit 435 allows user access to an implantable device feature according to the determined location and received user identity information. For example, the control circuit 435 may determine that the location of the external device is an operating room (OR), an emergency room (ER), a magnetic resonance imaging (MRI) clinic, or a general practice clinic. Together with the user identification information, the control circuit 435 can configure (e.g., selectively provide or limit) user access to implantable device features according to the location.

The locating circuit 430 can include one or more of software, firmware, and hardware to perform the functions described herein. In certain examples, the locating circuit 430 is integral to the control circuit 435. In some examples, a tablet computer or a cellular telephone is integrated into the external device 470, and the locating circuit 430 is included in the tablet computer or cellular telephone.

In some examples, the locating circuit 430 determines the location of the external device 470 using global positioning (e.g., a global positioning system (GPS), or assisted GPS). The communication signal may include one or more messages transmitted from satellites and the locating circuit 430 may determine the location of the external device 470 using the satellite transmission.

The locating circuit 430 may cross reference coordinates determined by global positioning with map information to determine that the coordinates are related to a hospital location or to a type of clinic for example. The map information may be stored in a memory circuit integral to, or electrically coupled to, the control circuit 435, or the map information may be stored in a remote server (e.g., a cloud server or cloud computer) accessed by the control circuit 435 using the communication circuit 425 or the port 455 (e.g., the port may be a universal serial bus (USB) interface) to access the Internet.

In some examples, the locating circuit 430 determines the location of the external device 470 using cellular phone tower (e.g., cell site) information. The communication circuit 425 may receive a communication signal transmitted from a cell tower. The received communication signal may identify the cell tower transmitting the signal and the locating circuit 430 determines the location of the external device 470 from the cell tower identification. The locating circuit 430 may cross reference the cell tower information with location information (e.g., using a lookup table) from the memory or from access to cloud computing resources to determine the location of the external device 470.

In some examples, the locating circuit 430 determines the location of the external device 470 using wireless fidelity (WiFi) network mapping. The communication circuit 425 may receive a communication signal transmitted by a wireless fidelity (WiFi) network. The received communication signal may identify the WiFi network the locating circuit 430 may include a cross reference of WiFi nodes or networks for one or more areas. The received communication signal may identify the WiFi node or network (e.g., using an internet protocol address), and the location can then be determined from the cross reference. In certain examples, the communication signal identifies a local area network (LAN) and the locating circuit 430 identifies the location of the external device 470 from the identification of the LAN.

In some examples, the locating circuit 430 uses a combination of two or more methods to identify the location of the external device. WiFi network or LAN information may provide intra-building information to the locating circuit 430. This information can help to further identify a function being performed at a location initially identified with GPS or cell tower information.

For instance, the communication circuit 425 may receive both a cell tower signal and a signal from a LAN network. The locating circuit 430 may identify a more general area using the cell tower signal (e.g., to identify that the external device is in a hospital) and identify a more specific area using the LAN signal (e.g., identify that the external device 470 is located in an operating theater or OR).

In some examples, when a location of the external device 470 is determined, the locating circuit 430 may identify a communication network associated with the determined location. The control circuit 435 may store an identifier for the communication network in the memory circuit in association with the determined location in the memory circuit 440. The locating circuit 430 can then deduce the location the next time an identifying signal is received from the communication network.

In some examples, the locating circuit 430 detects physical activity to determine if the location is changing or to adjust the location determination. The external device 470 may include an activity sensor 445 electrically coupled to the locating circuit. Some examples of an activity sensor include an accelerometer and a tilt switch. The locating circuit 430 estimates the location of the external device 470 according to the location determined using the received communication signal and subsequent motion sensed using the activity sensor. This may be useful to detect a change in the intra-building location of the external device 470.

The external device can receive the user identity information via the port 455, and the port 455 may include a communication port, or COMM port, to receive the user identity information. The COMM port may be a wired port or a wireless port. The COMM port may communicate using a standard protocol such as a USB protocol or firewire protocol.

In some examples, a user interface 450 is coupled to the port 455 to receive the user identity information. The user interface 450 may include one or more of a display, a mouse, a keyboard, and a touch sensitive or multi-touch sensitive display screen.

Using the port 455 to receive user identity information can also provide a level of security to accessing features of the implantable device. In some examples, the port 455 is coupled to a card reader that determines the user identity from an identification card of the user. The card reader may scan the identification card for information when the card is held before the card reader, or the identification card may be swiped through the card reader to provide the identity information. In some examples, the port 455 is coupled to a biometric scanner (e.g., a finger print scanner, a hand print scanner, etc.) and the port 455 receives biometric information of a user.

In some examples, a fourth device that is associated with the user identity information can be involved in obtaining the user identity information. The fourth device may be, among other things, a cellular telephone associated with the user, or a personal electronic device associated with the user that can access the internet. The communication circuit 425 may transmit access information receivable by the fourth device according to a telephone number or an IP address associated with the user identity information.

The fourth device may retransmit the access information back to the external device 470 where it is received by the communication circuit 425. The control circuit 435 verifies that the received access information corresponds to the transmitted access information and allows user access to the implantable device feature or features according to the verification.

The access information can be machine readable. In some examples, the external device 470 includes a scanning circuit 460 that may be coupled to the port 455. The scanning circuit 460 may optically read the access information, such as by reading a barcode. The communication circuit 425 may transmit a barcode receivable by a telephone (e.g., a smartphone) associated with the user identity information. The scanning circuit 460 scans the barcode displayed on the telephone and the control circuit 435 verifies that the scanned barcode is the same as the transmitted barcode.

In some examples, the external device 470 includes a camera or other imaging device. The control circuit 435 initiates the taking of an image (e.g., a photograph) of the user who is given access to the external device 470. The image may be included in a record of access to the external device 470.

It can be seen from the examples described herein that because functions required to be performed by an external device are often dependent upon location, determining the location with the external device can lead to simplification of user interaction with an implantable device. Including user identification to determine the interface can simplify user interaction as well provide security in accessing the implantable device features.

As explained previously herein, the control circuit 435 configures user access to one or more implantable device features according to the determined location and user identity information. The control circuit 435 may present (e.g., display) implantable device features on a user interface 450 as available to a user according to the determined location and received user identity information. For example, the features may be selectable via indications presented on one or more user interface menus. The control circuit 435 may exclude presentation by the user interface 450 of an implantable device feature limited by one or both of the determined location and the user identity information. Excluding a feature may include not presenting the feature on a displayed menu or ghosting the feature on the display to indicate that the feature is not available to the user.

For example, it may be desirable to suspend the delivery of defibrillation therapy to a patient who is in an ER of a hospital. In response to the locating circuit 430 determining that the location of the external device 470 is an ER and receiving information that the user is a physician, the control circuit 435 configures the user interface 450 to allow the user to enable or disable delivery of defibrillation therapy by the implantable device. The control circuit 435 may also allow the user to change a tachyarrhythmia detection rate of the implantable device in order to make the implantable device less sensitive to detection of tachyarrhythmia.

In another example, it may be desirable to place the implantable device in an electrocautery mode when the patient is undergoing surgery. In electrocautery mode, defibrillation or cardioversion therapy is disabled if the implantable device is an ICD. If the implantable device provides pacing therapy, electrocautery mode may include providing asynchronous pacing. In asynchronous pacing, the pacing pulses are delivered according to a timer and not according to sensed cardiac events. This prevents non-cardiac events (e.g., the electrocautery) that may be sensed by the implantable device from influencing the therapy being provided. In response to the locating circuit 430 determining that the location of the external device 470 is an OR and based on the user identity information, the control circuit 435 allows an approved user to initiate the electrocautery mode in the implantable device.

In certain examples, the control circuit 435 prevents access to implantable device features other than electrocautery mode when determining that the external device is in an ER. In certain examples, the control circuit 435 prevents access to the electrocautery mode (e.g., does not provide the electrocautery mode in the displayed menu) according to the received user identity information. In certain examples, the control circuit 435 allows some information stored in the implantable device to be read or uploaded from the implantable device by the user based on the determined location and the user identity information.

In another example, it may be desirable to place the implantable device in an MRI mode when the patient is to undergo magnetic resonance imaging. Similar to the electrocautery mode, defibrillation or cardioversion therapy can be disabled in the MRI mode to avoid noise from the MRI causing false positive indications of the need for therapy. The MRI mode may also involve asynchronous pacing, and the asynchronous pacing may be delivered at a rate that is higher than a determined intrinsic rate. Pacing at a rate higher than the intrinsic rate prevents the implantable device from pacing into an intrinsic depolarization due to the presence of noise.

In response to the locating circuit 430 determining that the location of the external device 470 is an MRI clinic and based on the user identity, the control circuit 435 configures the user interface 450 to allow an approved user to enable an MRI mode in the implantable device. In some examples, the control circuit 435 configures the user interface 450 to allow the user to initiate a device-automated pacing threshold test when it is determined that the external device 470 is located in an MRI clinic. In certain examples, the control circuit 435 does not allow user access to MRI mode or electrocautery mode, or these modes are disabled, unless the external device 470 is in an MRI clinic or OR, respectively. In certain examples, the control circuit 435 does not allow user access to MRI mode or electrocautery mode when the identity information identifies the user as a technical support specialist rather than a physician.

In some examples, in response to the locating circuit 430 determining that the location of the external device 470 is a general practice clinic and the identity information identifying the user as a physician or nurse, the control circuit 435 configures the user interface 450 to allow user read-only access to at least a portion of data or other information stored in the implantable device.

In some examples, the control circuit 435 presents or displays features as available on the user interface according to the determined location, the received user identity and the type of implantable device. For instance, services related to cardioversion and defibrillation are only presented if the implantable device has one or both of cardioversion and defibrillation capability.

For some locations, the control circuit 435 allows user access to substantially all of the features of the implantable medical device. For instance, if the locating circuit 430 determines that the external device is located in the office of a cardiologist or a cardiology clinic and the control circuit 435 determines that the user is a cardiologist, the control circuit 435 may allow user access to all programmable device parameters. In another example, if the control circuit 435 determines that the user is a manufacturer's representative, the control circuit 435 may allow access to all features of the implantable device regardless of the location of the external device 470. Some device capability, such as changing executable code in the implantable device may still not be allowed by the control circuit 435.

When the control circuit 435 detects a change in location of the external device (e.g., as indicated by the locating circuit 430), the control circuit 435 can change user access to one or more implantable device features according to the changed location and identity information. For instance, control circuit 435 may change the user interface presented to a user when the location is changed from an office to an OR even though the user information remains unchanged.

In some examples, the external device 470 is dedicated to a certain location. In other words, it is intended that the external device 470 only be used at a specified or approved location. When the locating circuit 430 determines that the location of the external device 470 is not at the approved location, the control circuit 435 may disable the external device 470 altogether (e.g., "brick" the device).

For various locations, such as an OR, ER, or MRI clinic, it may be desirable to turn one or both of tachyarrhythmia detection and cardioversion/defibrillation therapy off. There is a concern that the user of the external device 470 may leave the detection or therapy turned off when the patient leaves the location.

Figure 5:
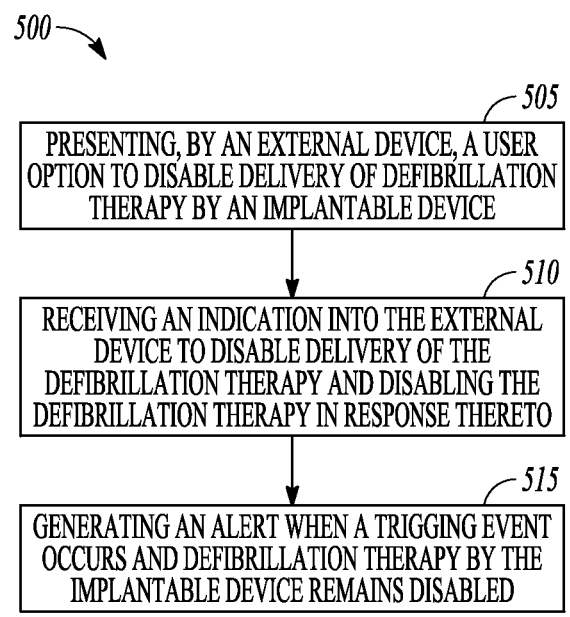
FIG. 5 is flow diagram of an example of a method for operating an external device that communicates with an implantable device.

FIG. 5 is flow diagram of an example of a method 500 for operating an external device that communicates with an implantable device. At block 505, a user option is presented by the external device (e.g., using a user interface) to disable delivery of defibrillation therapy by the implantable device.

At block 510, an indication is received into the external device to disable delivery of the defibrillation therapy. The defibrillation therapy is disabled in the implantable device in response to receiving the indication. At block 515, an alert is generated when a triggering event occurs and defibrillation therapy by the implantable device remains disabled. The alert may be generated by the external device or by a separate device that communicates the alert to the external device. The external device may then present the alert to the user.

Returning to the example of FIG. 4, the control circuit 435 can present a user option on the user interface 450 to disable delivery of one or both of defibrillation therapy and cardioversion therapy by the implantable device. The port 455 may receive an indication into the external device 470 to disable delivery of the defibrillation and/or cardioversion therapy.

The control circuit 435 communicates a disable of the therapy to the implantable device in response to receiving the indication. The disable may be a device command communicated using wireless telemetry. In response to the control circuit 435 detecting a triggering event, the control circuit 435 presents an alert to a user (e.g., using the user interface 450) when the triggering event occurs and defibrillation therapy by the implantable device remains disabled.

In some examples, the triggering event includes expiration of a timed duration. The external device 470 can include a timer circuit 465 electrically coupled to or integral to the control circuit 435. The control circuit 435 initiates timing of a specified (e.g., programmed) time duration by the timer circuit 465 in response to communication of the disable to the implantable device.

If the specified time duration expires and the defibrillation or cardioversion therapy by the implantable device remains disabled, the control circuit generates the alert and the alert is presented to the user. A complication to the approach can arise if the external device 470 is turned off or powered down. This could also turn off the timer circuit 465 and expiration of the timed duration would not be detected. In some examples, the control circuit 435 maintains circuit power to the timer circuit when the therapy is disabled until the defibrillation therapy by the implantable device is enabled or the alert is generated.

In some examples, the timing is done by a device different from the external device 470. In certain examples, the timing device is a server remote from the external device 470. The control circuit 435 may communicate an indication that delivery of defibrillation therapy is disabled to the remote server. When therapy is re-enabled using the external device 470, the control circuit 435 may communicate an indication to the remote server that delivery of defibrillation therapy is re-enabled. The control circuit 435 receives the alert from the remote server when the remote server fails to receive the indication that the delivery of defibrillation therapy is re-enabled a specified time duration after receiving the indication that delivery of defibrillation therapy is disabled. The control circuit 435 then presents the alert to the user.

In some examples, the control circuit 435 transmits a status that defibrillation/cardioversion therapy is disabled to a remote server. The remote server may track multiple implantable devices whose therapy is disabled, and may time durations for each of the implantable devices. For example, the remote server may store a table in memory for the implantable devices. The table may include an indication of therapy status as "off" when the therapy is disabled and therapy "on" when enabled or re-enabled. A timed duration can be initiated for any device whose status for one of the devices remains off when the timed duration for that device expires. The remote server may then send a reminder to a person, hospital, or clinic to re-enable the therapy.

In certain examples, the implantable device times the duration when the therapy is disabled. The control circuit 435 receives the alert from the implantable device when the control circuit fails to re-enable the delivery of defibrillation therapy after the specified time duration. The control circuit 435 then presents the alert to the user.

In certain examples, the control circuit 435 also transmits the alert that therapy was not re-enabled to a separate device such as a remote server. The remote server may send a reminder to a person, a hospital, or clinic to re-enable the therapy.

In some examples, the triggering event includes a change in location of the external device 470. According to the location or locations of the external device 470 determined by the locating circuit 430, the control circuit 435 generates the alert when determining that the location of the external device 470 has changed while defibrillation therapy by the implantable device remains disabled.

Detecting the disabling of one or both of defibrillation therapy and cardioversion therapy and providing a reminder to caregivers to re-enable the therapy, can prevent inadvertent disabling by caregivers allowing a patient to receive the full benefit of the therapy provided by the implantable device.

ADDITIONAL NOTES AND EXAMPLES

Example 1 can include subject matter (such as an apparatus) comprising an external device for communication with an implantable device. The external device can include: a communication circuit configured to receive a communication signal from at least a third device separate from the external device and the implantable device, a locating circuit configured to determine a location of the external device using the received communication signal, a port configured to receive user identity information into the external device, and a control circuit electrically coupled to the communication circuit, the locating circuit, and the port. The control circuit is configured to allow user access to an implantable device feature according to the determined location and received user identity information.

In Example 2, the subject matter of Example 1 optionally includes a communication circuit configured to transmit access information receivable by a fourth device that is associated with the user identity information, and receive the access information into the external device. The control circuit is optionally configured to verify that the received access information corresponds to the transmitted access information, and allow user access to the implantable device feature according to the verification.

In Example 3, the subject matter of one or any combination of Examples 1 and 2 optionally includes a scanning circuit. The communication circuit is optionally configured to transmit a barcode receivable by a telephone associated with the user identity information, the scanning circuit is optionally configured to scan a barcode displayed on the telephone, and the control circuit is optionally configured to verify that the scanned barcode is the same as the transmitted barcode.

In Example 4, the subject matter of one or any combination of Examples 1-3 optionally includes a port is configured to receive biometric information of a user.

In Example 5, the subject matter of one or any combination of Examples 1-4 optionally includes a camera. The control circuit is optionally configured to initiate obtaining an image of a user given access to the external device, and include the image in a record of access to the external device.

In Example 6, the subject matter of one or any combination of Examples 1-5 optionally includes a control circuit configured to detect a change in location of the external device, and change user access to one or more implantable device features according to the changed location and identity information.

In Example 7, the subject matter of one or any combination of Examples 1-6 optionally includes a control circuit configured to disable the external device when determining that the location of the external device is outside of an approved area for the user identity information.

In Example 8, the subject matter of one or any combination of Examples 1-7 optionally includes a locating circuit configured to determine the location of the external device using at least one of a global positioning system (GPS), wireless fidelity (WiFi) network mapping, cellular telephone tower identification, and local area network (LAN) identification.

Example 9 can include subject matter (such as a method, a means for performing acts, or a machine-readable medium including instructions that, when performed by the machine, cause the machine to perform acts), or can optionally be combined with the subject matter of one or any combination of Examples 1-8 to include such subject matter, comprising: receiving a wireless communication signal using an external device (the external device is configured to communicate with an implantable device and receive the wireless communication signal from at least a third device), determining, by the external device, a location of the external device according to the received communication signal, receiving user identity information into the external device, and configuring, by the external device, user access to an implantable device feature according to the determined location and received user identity information.

Such subject matter can include means for receiving a wireless communication signal using an external device, an illustrative example of which include a communication circuit configured to communicate wirelessly with one or more of a LAN, a cellular telephone network, a GPS, or a proprietary medical device telemetry system or circuit. Such subject matter can include means for determining a location of the external device according to the received communication signal, an illustrative example of which is a locating circuit included in the external device. Such subject matter can include means for receiving user identity information into the external device, an illustrative example of which includes a port such as a COMM port, that communicates serially using a standard protocol such as a USB protocol or firewire protocol, or a parallel COMM port. Such subject matter can include means for configuring user access to an implantable device feature according to the determined location and received user identity information, an illustrative example of which is a control circuit that can include a microprocessor, a digital signal processor, application specific integrated circuit (ASIC), or other type of processor.

In Example 10, the subject matter of Example 9 optionally includes transmitting access information, associated with the user identity information, receivable by a fourth device, receiving the access information into the external device, and verifying that the received access information corresponds to the transmitted access information.

In Example 11 the subject matter of one or any combination of Examples 9 and 10 optionally includes receiving biometric information of a user into the external device.

In Example 12, the subject matter of one or any combination of Examples 9-11 optionally includes determining that the location of the external device has changed, and reconfiguring the user access according to the changed location and user identity information.

Example 13 includes subject matter (such as an apparatus), or can optionally be combined with the subject matter of one or any combination of Examples 1-12 to include such subject matter, comprising an external device. The external device can include: a communication circuit configured to communicate with an implantable device, a user interface, a control circuit electrically coupled to the user interface and communication circuit and configured to present a user option to disable delivery of defibrillation therapy by the implantable device, a port configured to receive an indication into the external device to disable delivery of the defibrillation therapy. The control circuit is also configured to communicate a disable of the defibrillation therapy to the implantable device in response to receiving the indication, detect a triggering event, and present an alert to a user when the triggering event occurs and defibrillation therapy by the implantable device remains disabled.

In Example 14, the subject matter of Example 13 optionally includes a timer circuit electrically coupled to or integral to the control circuit. The control circuit is optionally configured to: initiate timing of a specified time duration by the timer circuit in response to communication of the disable to the implantable device, generate the alert when the specified time duration expires and the defibrillation therapy by the implantable device remains disabled, and maintain circuit power to the timer circuit until at least one of the defibrillation therapy by the implantable device is enabled or the alert is generated.

In Example 15, the subject matter of Example 13 optionally includes a control circuit configured to: communicate an indication that delivery of defibrillation therapy is disabled to a server remote from the external device, communicate an indication that delivery of defibrillation therapy is re-enabled to the remote server, and receive the alert from the remote server when the remote server fails to receive the indication that the delivery of defibrillation therapy is re-enabled a specified time duration after receiving the indication that delivery of defibrillation therapy is disabled.

In Example 16, the subject matter of Example 13 optionally includes a control circuit configured to receive the alert from the implantable device when the control circuit fails to re-enable the delivery of defibrillation therapy after a specified time duration.

In Example 17, the subject matter of one or any combination of Examples 13-16 optionally includes a locating circuit configured to determine a location of the external device, and the control circuit is optionally configured to generate the alert when determining that the location of the external device has changed while defibrillation therapy by the implantable device remains disabled.

Example 18 can include subject matter (such as a method, a means for performing acts, or a machine-readable medium including instructions that, when performed by the machine, cause the machine to perform acts), or can optionally be combined with the subject matter of one or any combination of Examples 1-17 to include such subject matter, comprising: presenting a user option to disable delivery of defibrillation therapy by an implantable device, wherein the external device is configured to communicate with the implantable device, receiving an indication into the external device to disable delivery of the defibrillation therapy and disabling the defibrillation therapy in response thereto, and generating an alert when a triggering event occurs and defibrillation therapy by the implantable device remains disabled.

Such subject matter can include means for presenting a user option to disable delivery of defibrillation therapy by an implantable device, an illustrative example of which includes a user interface on the external device or a separate device and the user interface having a display. Such subject matter can include means for communicating with the implantable device, an illustrative example of which includes a far-field radio frequency transceiver or a near field inductive telemetry circuit. Such subject matter can include means for receiving an indication into the external device to disable delivery of the defibrillation therapy, an illustrative example of which includes a port such as a COMM port, that communicates serially using a standard protocol such as a USB protocol or firewire protocol, a parallel COMM port, or a port connected to a user interface having a mouse or keypad. Such subject matter can include means for disabling the defibrillation therapy, an illustrative example of which includes a control circuit that includes logic circuits, a microprocessor, a digital signal processor, application specific integrated circuit (ASIC), or other type of processor. Such subject matter can include means for generating an alert when a triggering event occurs and defibrillation therapy by the implantable device remains disabled, an illustrative example of which includes a control circuit.

In Example 19, the subject matter of Example 18 can optionally include initiating a timer circuit of the remote server in response to the received indication, and communicating the alert from the remote server to the external device and presenting the alert to a user via the external device. The triggering event can optionally include a timeout of the timer circuit of the remote server while defibrillation therapy by the implantable device remains disabled.

In Example 20, the subject matter of Example 18 optionally includes determining, by the external device, a location of the external device. The triggering event optionally includes the external device determining that the location has changed while defibrillation therapy by the implantable device remains disabled.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An external device for communication with an implantable device, the external device comprising:
   a communication circuit configured to receive a communication signal from at least a third device separate from the external device and the implantable device;
   a locating circuit configured to determine a location of the external device using the received communication signal;
   a port configured to receive user identity information into the external device, wherein first user identity information received at the port allows access to a different set of device features than second user identity information; and
   a control circuit electrically coupled to the communication circuit, the locating circuit, and the port, wherein the control circuit is configured to reconfigure a device user interface to change user access to an implantable device feature according to the determined location and received user identity information.

2. The external device of claim 1,
   wherein the communication circuit is configured to:
      transmit access information receivable by a fourth device that is associated with the user identity information; and
      receive the access information into the external device, and
   wherein the control circuit is configured to:
      verify that the received access information corresponds to the transmitted access information; and
      allow user access to the implantable device feature according to the verification.

3. The external device of claim 2, including a scanning circuit,
   wherein the communication circuit is configured to transmit a barcode receivable by a telephone associated with the user identity information,
   wherein the scanning circuit is configured to scan a barcode displayed on the telephone, and
   wherein the control circuit is configured to verify that the scanned barcode is the same as the transmitted barcode.

4. The external device of claim 1, wherein the port is configured to receive biometric information of a user.

5. The external device of claim 1, including a camera, wherein the control circuit is configured to:
   initiate obtaining an image of a user given access to the external device; and include the image in a record of access to the external device.

6. The external device of claim 1, wherein the control circuit is configured to:
   detect a change in location of the external device; and
   change user access to one or more implantable device features according to the changed location and identity information.

7. The external device of claim 1, wherein the control circuit is configured to disable the external device when determining that the location of the external device is outside of an approved area for the user identity information.

8. The external device of claim 1, wherein the locating circuit is configured to determine the location of the external device using at least one of a global positioning system (GPS), wireless fidelity (WiFi) network mapping, cellular telephone tower identification, and local area network (LAN) identification.

* * * * *